United States Patent [19]

Ritter

[11] Patent Number: 5,069,233
[45] Date of Patent: Dec. 3, 1991

[54] METHOD AND APPARATUS FOR REMOVING DEBRIS FROM BETWEEN AND AROUND TEETH

[76] Inventor: Charles H. Ritter, 3219 Thomasville Rd.; #17A, Tallahassee, Fla. 32312

[21] Appl. No.: 605,441

[22] Filed: Oct. 30, 1990

[51] Int. Cl.⁵ .............................................. A61C 15/00
[52] U.S. Cl. ...................................... 132/322; 132/323
[58] Field of Search ............... 132/322, 323, 324, 325, 132/326, 327; 15/22.1

[56] References Cited

U.S. PATENT DOCUMENTS

| | | | |
|---|---|---|---|
| 1,475,986 | 12/1923 | Cooke | 132/324 |
| 3,378,017 | 4/1968 | Stiles | 132/324 |
| 3,421,524 | 1/1969 | Waters | 132/322 |
| 3,472,247 | 10/1969 | Borsum et al. | 132/322 |
| 3,534,745 | 10/1970 | Waters | 132/322 |
| 3,759,274 | 9/1973 | Warner | 132/322 |
| 3,847,167 | 11/1974 | Brien | 132/322 |
| 3,927,686 | 12/1975 | Zambito . | |
| 4,014,354 | 3/1977 | Garrett | 132/322 |
| 4,235,253 | 11/1980 | Moore | 132/322 |
| 4,245,658 | 1/1981 | Lecouturier | 132/322 |
| 4,265,257 | 5/1981 | Salyer | 132/322 |
| 4,307,740 | 12/1981 | Florindez et al. | 132/322 |
| 4,333,197 | 6/1982 | Kuris . | |
| 4,338,957 | 7/1982 | Melbauer | 132/322 |
| 4,458,702 | 7/1984 | Grollimund | 132/322 |
| 4,605,025 | 8/1986 | McSpadden | 132/322 |
| 4,698,869 | 10/1987 | Mierau et al. . | |
| 4,706,695 | 11/1987 | Urso | 132/322 |
| 4,727,894 | 3/1988 | Melbauer | 132/322 |
| 4,736,757 | 4/1988 | Badoux | 130/323 |
| 4,830,032 | 5/1989 | Jousson | 132/323 |
| 5,016,660 | 5/1991 | Boggs | 132/322 |
| 5,020,179 | 6/1991 | Scherer . | |

Primary Examiner—Gene Mancene
Assistant Examiner—Michael Lynch
Attorney, Agent, or Firm—Shlesinger, Arkwright & Garvey

[57] ABSTRACT

A preferred embodiment of the present invention is directed to an automatic dental flosser having a housing which includes a handle and an operating head. The operating head includes a pair of hollow tines which extend in a first plane. A flossing assembly is operably associated with the operating head for removing debris from between and around teeth. The flossing assembly includes a support member for supporting a flossing material. A first portion of the support member is disposed in the hollow tines while a second portion of the support member is removed therefrom. A drive member is operably associated with the first portion of the flossing assembly for linearly displacing the support member. A stop is provided intermediate the upper and lower surfaces of the hollow tines for regulating the proximity of the flossing material to the oral tissues of an individual. Further, an adjustable protective cover encases the second portion of the support member which is removed from the hollow tines.

27 Claims, 4 Drawing Sheets

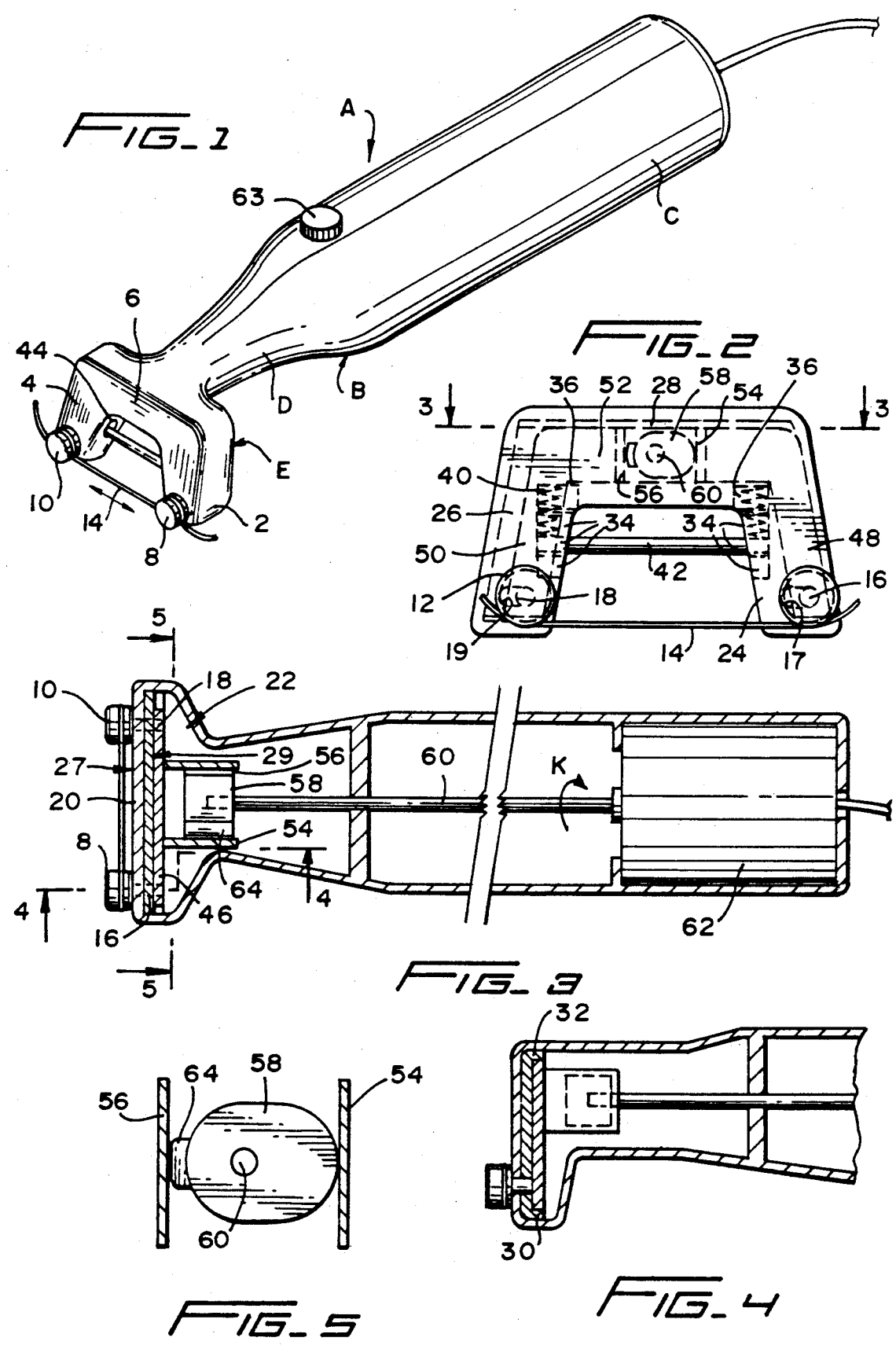

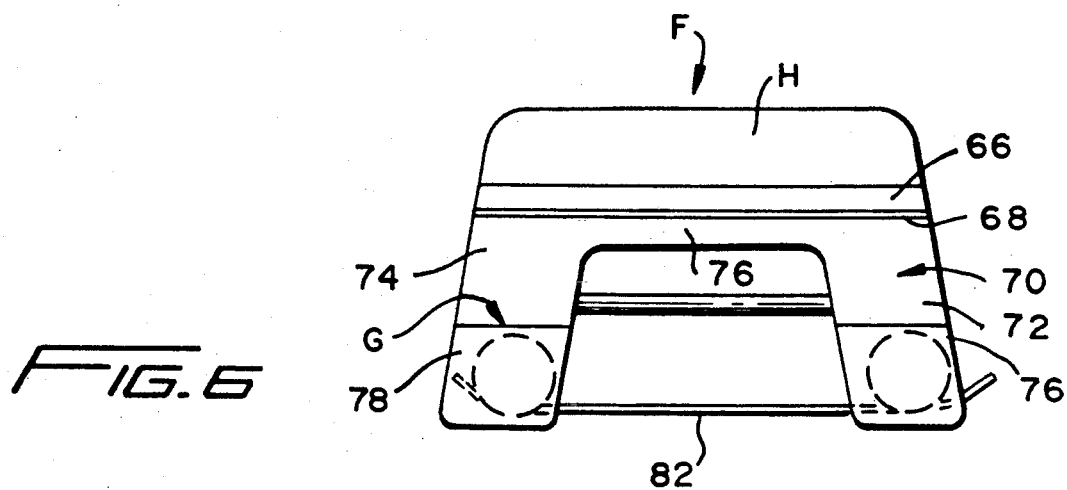
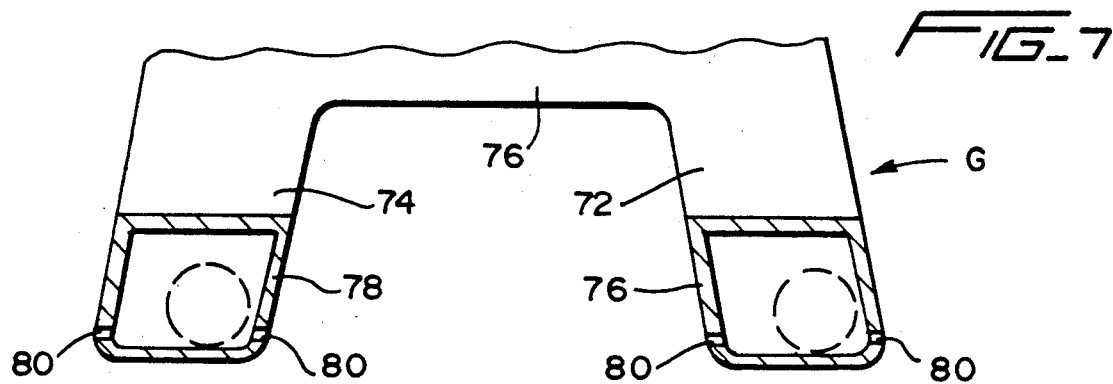
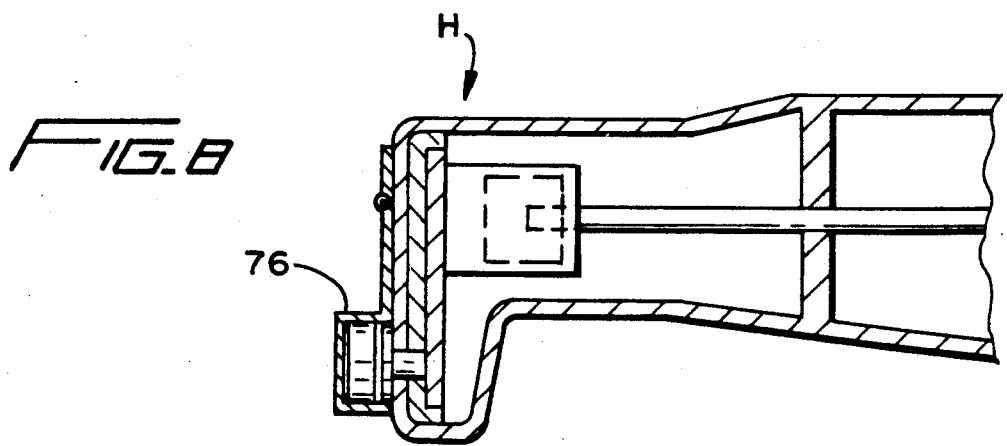

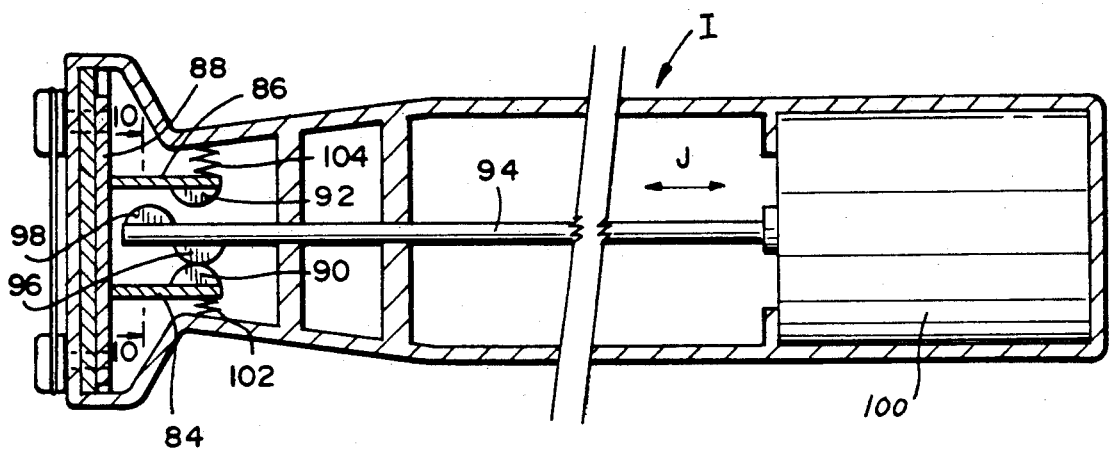
FIG_9
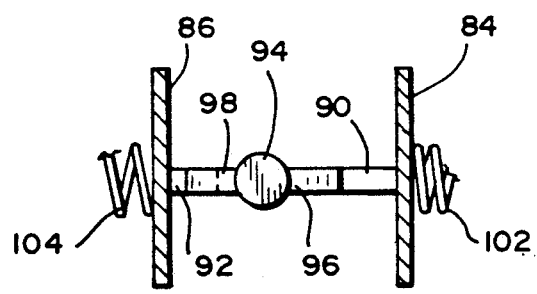
FIG_10

METHOD AND APPARATUS FOR REMOVING DEBRIS FROM BETWEEN AND AROUND TEETH

FIELD OF THE INVENTION

The present invention is directed generally to implements for aiding individuals in practicing proper dental hygiene. More specifically, a preferred embodiment of the present invention is directed to an automatic dental flosser for removing debris located around and lodged between an individual's teeth.

BACKGROUND OF THE PRESENT INVENTION

The importance of practicing proper dental hygiene has been well documented. In this regard, it is extremely advantageous to frequently and systematically remove plaque and debris from around and between an individual's teeth. Failure to religiously remove debris and plaque from between and around teeth is likely to lead to dental disease including tooth decay, gingivitis and the like.

Countless configurations of toothbrushes have been proposed to remove plaque. However, it is widely accepted by dentists periodontists and dental hygienists, that it is not possible to reach a number of remote areas of dental sulcuses by using a toothbrush alone. Dental floss or tape has been used to remove plaque from these hard to reach areas. The conventional process of flossing teeth manually with dental floss or tape has numerous disadvantages. Specifically, flossing is time consuming and extremely tedious. Moreover, manual flossing requires a level of dexterity beyond that of many individuals. For example, it is extremely difficult and/or painful for handicapped persons and those suffering from arthritis and similar ailments to manually floss their teeth.

Several implements have been proposed to overcome the disadvantages associated with the aforementioned manual method of flossing teeth. The following U.S. patents are directed to implements of this nature: U.S. Pat. Nos. 3,421,524; 3,472,247; 3,534,745; 3,759,274; 3,847,167; 4,014,354; 4,235,253; 4,245,658; 4,265,257; 4,338,957; 4,458,702; 4,605,025; 4,706,695; 4,727,894; and 4,830,032. The dental flossers described in the these U.S. patents have several inherent disadvantages. Generally speaking, previously known dental flossers are extremely complex. As a result, these devices are laborious and expensive to manufacture. Moreover, their complex construction makes servicing such devices difficult. Further, previously known automatic flossers include at least one exposed reciprocating element which upon coming into contact with sensitive oral tissues will likely cause an individual discomfort.

A significant number of prior dental flossers are designed such that the flossing material traverses an arcuate path. An individual using such a device must exercise caution, since movement of these types of flossers in either a vertical or horizontal direction may result in the flossing material rubbing sensitive oral tissues. Therefore, an individual is likely to restrict movement of such devices. Because such devices can not be readily moved in a vertical or horizontal direction, it is extremely more likely that hard to reach areas will be missed.

Some previously known flossers have included a flossing material which moves linearly. Flossers of this type commonly employ complex feeding systems for the floss or alternatively require a specialized flossing material which must be replaced after every use.

Finally, it is noted that conventional dental flossers do not include any means for restricting the proximity of the dental floss material with respect to the surrounding oral tissues. Therefore, if conventional flossers are improperly used offensive touching of the flossing material against the oral tissues may occur.

OBJECTS AND SUMMARY OF THE PRESENT INVENTION

It is an object of the present invention to provide a new and improved apparatus and method for removing debris from between and around teeth.

It is another object of the present invention to provide an apparatus for removing debris from between and around teeth which includes a housing having a handle and an operating head, the operating head extends in a first plane and includes a pair of hollow tines. A flossing means is operably associated with the operating head for removing debris from between and around teeth. The flossing means includes a support member for supporting a flossing material and at least a portion of the support member is disposed in the hollow tines. Drive means is operably associated with the flossing means for displacing the portion of the support member disposed in the housing in a plane substantially parallel to the first plane.

Among other advantages, a dental implement formed in the manner described above reduces the discomfort experienced by an individual in the use thereof. Specifically, the hollow tines engage at least a portion of the support member thereby reducing an individual's exposure to reciprocating elements.

A further object of the present invention is to provide an apparatus for removing debris from between and around teeth which comprises a main body member having first and second ends and an operating head which extends in a first plane at an angle to the main body member and disposed adjacent the first end thereof. Flossing means is operably associated with the operating head for removing debris from between and around teeth. The flossing means includes a support member for supporting a flossing material such that at least a portion of the flossing material extends at an angle to the main body member. A drive is operably associated with the flossing means for displacing the support member in a plane substantially parallel to the first plane.

A dental flosser designed to support a flossing material as recited above is advantageous for a number of reasons, one of which is remote dental sulcuses can be readily reached thereby.

Yet another object of the present invention is to provide an apparatus for removing debris from between and around teeth which includes a main body member having first and second ends and an operating head disposed adjacent the first end of the main body member. Flossing means is operably associated with the operating head for removing debris from between and around teeth. The flossing means includes a support member for supporting a flossing material. A drive means is operably associated with the flossing means for linearly displacing the support member in at least a first direction. The drive means includes an output shaft extending at an angle to the first direction and substantially parallel to the main body member.

A flosser having a drive means as described above for linearly displacing a support member can be readily displaced relative to the teeth in either a vertical or horizontal direction with minimal likelihood of offensive contact with the surrounding oral tissues. Moreover, this arrangement obviates the need for complex flossing feed systems and specialized flossing material.

Still another object of the present invention is to provide an apparatus for removing debris from between and around teeth which comprises a main body member having first and second ends, an operating heading disposed adjacent the first end of the main body member and which includes upper and lower surfaces. A flossing means is operably associated with the operating head for removing debris from between and around teeth. A drive means displaces the flossing means in at least a first direction. A stop means is provided to restrict movement of the flossing means relative to the teeth of an individual. The stop means is disposed intermediate the upper and lower surfaces of the operating head.

The apparatus described above is a significant improvement over previously known devices. In this regard, the stop means regulates the proximity of the flossing material to sensitive oral tissues thereby minimizing the contact between the flossing material and the oral tissues.

Yet still another object of the present invention is to provide an apparatus for removing debris from around and between teeth which includes a main body member having first and second ends, an operating head disposed adjacent the first end of the main body member and flossing means operably associated with the operating head for removing debris from between and around teeth. The flossing means includes a support member for supporting a flossing material. A drive means is operably associated with the flossing means for displacing the support member in at least a first direction. A shielding means is hingedly connected to the operating head for shielding the support member. The shielding means is adapted to be moved between a first position in which the shielding means covers the support member and a second position in which the shielding means is removed from the support member.

A dental implement formed in the manner described above is advantageous for several reasons, one of which is the shielding means acts to isolate the moving support member from the oral tissues. This is desirable because it substantially reduces the discomfort of the individual when using the dental implement.

These and other objects and advantages of the present invention will be readily apparent from the following detailed description of the invention.

In summary, a preferred embodiment of the present invention is directed to an automatic dental flosser having a housing which includes a handle and an operating head. The detachable and interchangeable operating head includes a pair of hollow tines which extend in a first plane. A flossing means is operably associated with the operating head for removing debris from between and around teeth. The flossing means includes a support member for supporting a flossing material. A first portion of the support member is disposed in the hollow tines while a second portion is removed therefrom. A drive means is operably associated with the first portion of the flossing means for linearly displacing the support member. A stop means is provided intermediate the upper and lower surfaces of the hollow tines for regulating the proximity of the flossing material to the oral tissues of an individual. Further, an adjustable protective cover encases the second portion of the support member which is removed from the hollow tines.

DETAILED DESCRIPTION OF THE DRAWINGS

FIG. 1 is a perspective view of a first preferred embodiment of the present invention.

FIG. 2 is a side elevational view of the embodiment illustrated in FIG. 1 with portions shown in phantom.

FIG. 3 is a fragmentary cross-sectional view taken along lines 3—3 in FIG. 2.

FIG. 4 is a fragmentary cross-sectional view taken along lines 4—4 in FIG. 3.

FIG. 5 is a cross-sectional view taken along lines 5—5 in FIG. 3.

FIG. 6 is a side elevational view of a second preferred embodiment of the present invention with portions shown in phantom.

FIG. 7 is a fragmentary rear elevational view of the protective cover illustrated in FIG. 6 with portions shown in section and phantom.

FIG. 8 is a fragmentary cross-sectional view of the embodiment illustrated in FIG. 6.

FIG. 9 is a fragmentary cross-sectional view of a third preferred embodiment of the present invention.

FIG. 10 is a cross-sectional view taken along lines 10—10 in FIG. 9.

DETAILED DESCRIPTION OF THE INVENTION

Figure 11:
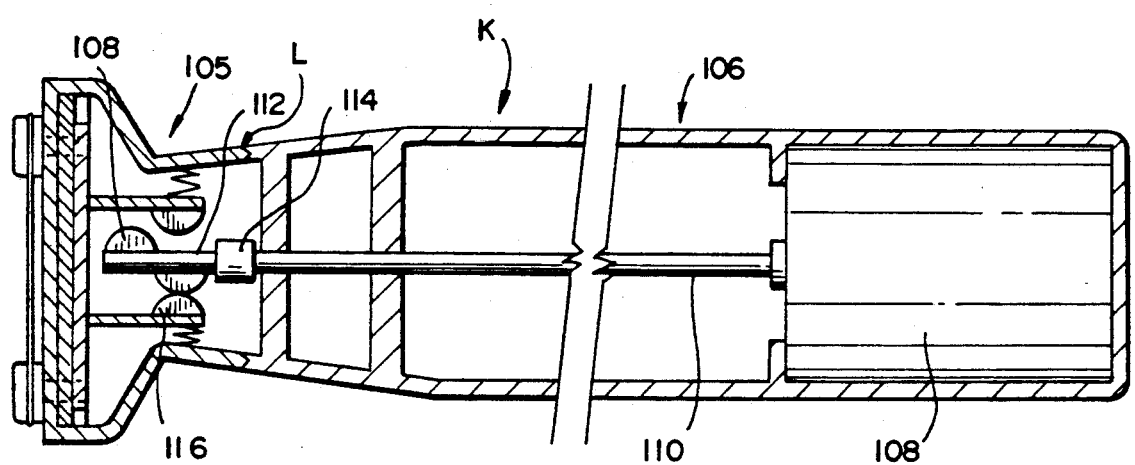
FIG. 11 is a cross-sectional view of a fourth preferred embodiment of the present invention.

The preferred embodiments of the present invention will be described hereinafter.

FIGS. 1 THROUGH 5

The first preferred embodiment of the present invention will be discussed below with reference made to FIGS. 1 through 5.

Referring to FIG. 1, an automatic dental flosser A includes a housing B. The housing B has a handle portion C, a neck portion D and an operating head E. The handle portion C has a substantially cylindrical configuration. Although not shown, it will be readily appreciated that undulations or other means may be formed in the underside of handle portion C to facilitate handling of the automatic dental flosser A by an individual. The neck D is tapered in the direction of operating head E. The operating head E is disposed substantially perpendicular to the longitudinal axis of handle C.

The operating head E includes a pair of hollow tines 2 and 4. A horizontally extending section 6 connects vertically oriented tine 2 to tine 4. The tines 2 and 4 extend downwardly and outwardly from section 6. A pair of knobs 8 and 10, each having a substantially cylindrical configuration, is positioned adjacent the lower portions of hollow tines 2 and 4, respectively. Each of the knobs 8 and 10 include an annular recess 12 (see FIG. 2) for receiving the dental floss or tape 14. Referring to FIG. 3, cylindrical pins 16 and 18 are fixed to knobs 8 and 10, respectively and are formed from a resilient material in order to provide tension on the floss 14. More specifically, the dental floss 14 is tightly wrapped around each of the knobs 8 and 10 to bias said knobs inwardly toward each other. This arrangement avoids slack from forming in dental floss 14 after repeated use thereof. In this regard, any movement of dental floss 14 will in turn cause pins 8 and 10 to move away from each other thereby maintaining the floss 14 taught.

A retaining plate 20 is positioned in the hollow cavity 22 of operating head E. The retaining plate 20 includes a pair of legs 24 and 26 and a horizontally extending connecting section 28, as seen in FIG. 2. Retaining plate 20 includes a front surface 27 and rear surface 29. Preferably, the rear surface 29 is machined to have a bearing surface. A first lip 30, as best shown in FIG. 4, extends from the bottom edge of each of the legs 26 and 28. A second lip 32 extends from the upper edge of connecting section 28. The lips 30 and 32 provide the retaining plate 20 with a substantially C-shaped profile.

Three horizontally extending openings 34 are formed in each of the legs 24 and 26 of retaining plate 20. A vertically extending channel 36 passes through each of the horizontally extending openings 34 in legs 24 and 26. Springs 38 and 40 are positioned in the channels 36. A bar 42 extends between the legs 24 and 26 of retaining plate 20 and the ends thereof are received and aligned in two of the openings 34. The bar 42 has a substantially continuous diameter which is smaller than that of openings 34. The springs 38 and 40 bias the bar 42 downwardly. The bar 42 may be made of a flexible material so that it can be readily inserted into different sets of openings 34, thereby varying the distance between the bar 42 and dental floss 14. The tines 2 and 4 each have an elongated slot 44 (only one of which is shown in FIG. 1) which extends substantially in a vertical direction from the lowermost to the uppermost opening 34.

It will be readily appreciated that bar 42, having a diameter smaller than openings 34 is permitted to move therein if acted upon by a force sufficient to overcome springs 38 and 40. However, the openings 34 prevent the bar 42 from moving a distance which is greater than the difference in the diameters of the openings 34 and bar 42. A slidable plate 46 is positioned directly adjacent to retaining plate 20 and is supported by legs 30 and 32 thereof. The bar 42 controls the depth which the floss 14 may be disposed between adjacent teeth.

Slidable plate 46, as best shown in FIG. 3, includes a pair of legs 48 and 50 and a horizontally extending section 52, as best shown in FIG. 2. Pins 16 and 18 are fixed to legs 48 and 50, respectively. Elongated horizontal slots 17 and 19 are formed in tines 2 and 4 respectively, and legs 26 and 28 of plate 20 to permit the pins 16 and 18 to move in a horizontal direction.

A pair of walls 54 and 56 are fixed to and extend rearwardly from slidable plate 46 at an upper portion thereof. The walls 54 and 56 extend substantially parallel to each other. Referring to FIG. 5, an elongated disc 58 is disposed intermediate walls 54 and 56. Output shaft 60 is eccentrically connected to disc 58. A conventional motor 62 rotates output shaft 60 in the direction indicated by arrow K. A counterweight 64 is secured to the disc 58 to reduce vibrations which might result from the eccentric connection between output shaft 60 and disc 58.

It will be readily appreciated that upon rotation of output shaft 60, the slidable plate 46 will move back and forth in a linear path within the hollow cavity 22 of operating head E imparting the same motion through knobs 8 and 10 to dental floss 14. Preferably, the motor 62 is powered by either a battery or an alternating current potential with a cord and plug arrangement. However, other power sources may be used to drive motor 62. A speed control 63, such as a variable rheostat, is operably connected to motor 62 for varying the speed of rotation of output shaft 60, as seen in FIG. 1.

FIGS. 6 THROUGH 8

A second embodiment of the present invention will now be described with reference made to the above-identified figures.

Referring to FIGS. 6 through 8, an automatic dental flosser F is depicted which is identical in configuration to that of dental flosser A and further includes a protective cover G hingedly connected to the front face of operating head H. The protective cover G includes a first plate 66, a hinge 68 and a second plate 70. The first plate 66 is fixed to the operating head G by conventional fastener means. The second plate 70 is rotatably connected to hinge 68 such that the second plate 70 can be rotated 180° from its operating position (shown in FIG. 8) to a storage position not shown. The second plate 70 includes a pair of legs 72 and 74 and an intermediate horizontally extending section 76. Casings 76 and 78 are formed in the lower surfaces of each of the legs 72 and 74 for receiving knobs 8 and 10. The casings 76 and 78 include aligned recesses 80 for receiving the dental floss 82. The casings 76 and 78 have a width greater than that of the diameter of knobs 8 and 10 to permit the knobs 8 and 10 to move in a horizontal direction therein.

It will be readily evident from the above description and the accompanying drawings that all reciprocating elements of the automatic dental flosser F are thereby encased, with the exception of the dental floss 82. Thus, the only moving part to which an individual is exposed is the floss. The dental floss 82 may be readily replaced by lifting protective cover G and substituting a new piece of floss for the used piece.

FIGS. 9 AND 10

A third embodiment of the present invention will be described hereinafter with reference made to the above identified figures.

Referring to FIG. 9, an automatic dental flosser I is constructed in a similar manner to that of dental flosser A and, therefore, only the differences will be discussed hereinafter. Walls 84 and 86 extend from slidable plate 88 and include cam surfaces 90 and 92. The cam surfaces 90 and 92 are aligned in the vertical direction. Output shaft 94 includes cam surfaces 96 and 98. The cam surfaces 96 and 98 are spaced from each other in a horizontal direction and lie on a common plane. Motor 100 linearly and reciprocally displaces the output shaft 94 as illustrated by arrow J. It will be readily appreciated that as the output shaft 94 moves to the right, as viewed in FIG. 9, cam surface 98 will engage cam surface 92 for forcing slidable plate 88 upward, as viewed in FIG. 9. Cam surface 96 in turn will move to the right out of engagement with cam surface 90. Upon movement of the output shaft 94 to the left, cam surface 96 reengages cam surface 90 and cam surface 98 moves to the left out of engagement with cam surface 92. Thus, the slidable plate 88 moves downward, as viewed in FIG. 9.

Referring to FIG. 10, a pair of springs 102 and 104 are positioned adjacent walls 84 and 86, respectively. The springs 102 and 104 minimize the vibration of dental flosser I resulting from movement of slidable plate 88.

FIG. 11

A fourth preferred embodiment of the present invention will now be described with reference made to the above-identified figure.

Referring to FIG. 11, a dental flosser K is constructed in a similar manner to that of flosser I in FIGS. 9 and 10. The dental flosser K includes an operating head 105 detachably connected to body member 106 at L by conventional means. Motor 108, identical to motor 100, is disposed in body member 106. An output shaft 110 is driven by motor 108 in the same manner as output shaft 94. Shaft 112 is detachably connected to output shaft 110 via sleeve 114. The shaft 112 includes cam surfaces 114 and 116 which are identical to cams 96 and 98, respectively. This embodiment permits an individual to readily detach operating head 105 and shaft 112 from the body member 106 to substitute another dental implement such as a toothbrush therefor.

While this invention has been described as having a preferred design, it is understood that it is capable of further modifications, uses and/or adaptions of the invention following in general the principle of the invention including such departures from the present disclosure as come within the known or customary practice in the art to which the invention pertains, and as may be applied to the central features set forth and fall within the scope of the invention and the limits of the appended claims.

I claim:

1. An apparatus for removing debris from between and around teeth, comprising:
   a) a housing having a handle and an operating head, said operating head including a pair of hollow tines;
   b) flossing means operably associated with said operating head for removing debris from between and around teeth, said flossing means including a support member for supporting a flossing material to extend in a first direction between the pair of hollow tines and at least a portion of said support member being disposed in said hollow tines; and,
   c) drive means operably associated with said flossing means for displacing said portion of said support member disposed in said housing in the first direction.

2. An apparatus as in claim 1, wherein:
   a) said operating head extends substantially perpendicular to said handle;
   b) each of said hollow tines include an elongated slot formed therein; and,
   c) said support member includes a first plate and first and second pins, said first and second pins extend through corresponding elongate slots firmed in said hollow tines and are fixed to said first plate.

3. An apparatus as in claim 2, wherein:
   a) first and second knobs are operably connected to said first and second pins and said first and second knobs each include a recess for receiving a flossing material;
   b) a retaining plate having a substantially C-shaped configuration, said retaining plate includes an inner surface and an outer surface and said outer surface being disposed in abutting contact with said housing; and,
   c) said first plate is disposed in abutting contact with said inner surface of said retaining plate.

4. An apparatus as in claim 2, wherein:
   a) said drive means includes an output shaft extending substantially perpendicular to said operating head and means for rotating said output shaft; and,
   b) cam means operably connected to said first plate and said output shaft for linearly displacing said first plate upon rotation of said output shaft.

5. An apparatus as in claim 2, wherein:
   a) said drive means includes an output shaft extending substantially perpendicular to said operating head and means for linearly displacing said output shaft; and,
   b) cam means operably connected to said output shaft and said first plate for linearly displacing said first plate in a direction substantially perpendicular to a direction of movement of said output shaft.

6. An apparatus as in claim 1, wherein:
   a) said operating head and said handle are formed from a single piece.

7. An apparatus as in claim 1, wherein:
   a) said support member includes at least one resilient element for maintaining the flossing material taught, said resilient element being adapted to be initially biased inwardly by the flossing material.

8. An apparatus for removing debris from between and around teeth, comprising:
   a) a main body member having first and second ends;
   b) an operating head being disposed adjacent said first end of said main body member and extending at an angle to said main body member, said operating head including a pair of tines;
   c) flossing means operably associated with said operating head for removing debris from between and around teeth, said flossing means including a support member for supporting a flossing material such that at least a portion of the flossing material extends in a first direction between said pair of tines and at an angle to said main body member; and,
   d) drive means operably associated with said flossing means for displacing said support member linearly in the first direction.

9. An apparatus as in claim 8, wherein:
   a) said operating head extends substantially perpendicular to said main body member; and,
   b) said support member is adapted to support a flossing material substantially perpendicular to said main body member.

10. An apparatus as in claim 8, wherein:
   a) said operating head includes a hollow cavity and an external surface removed from said hollow cavity; and
   b) at least a first portion of said support member is positioned in said hollow cavity.

11. An apparatus as in claim 10, wherein:
   a) a second portion of said support member is positioned adjacent said external surface of said operating head and removed from said hollow cavity.

12. An apparatus as in claim 11, wherein:
   a) said second portion is adapted to support a flossing material removed from said hollow cavity.

13. An apparatus for removing debris from between and around teeth, comprising:
   a) a main body member having first and second ends;
   b) an operating head being disposed adjacent said first end of said main body member, said operating head including a pair of tines;
   c) flossing means operably associated with said operating head for removing debris from between and around teeth, said flossing means including a support member for supporting a flossing material, at least a portion of said support member extends between said pair of tines and at an angle to said main body member; and, d) a drive means operably associated with said flossing means for linearly displacing said support member in at least a first direction, said drive means having an output shaft extending at an angle to the first direction and substantially parallel to said main body member.

14. An apparatus as in claim 13, wherein:
a) said drive means includes means for rotating said output shaft; and,
b) cam means disposed intermediate said output shaft and said support member.

15. An apparatus as in claim 14, wherein:
a) first and second walls are secured to said support member; and,
b) said cam means is disposed in abutting engagement with said first and second walls.

16. An apparatus as in claim 15, wherein:
a) said cam means includes a counter weight means for damping vibrations of the apparatus.

17. An apparatus as in claim 13, wherein:
a) said drive means includes means for linearly displacing said output shaft in a first direction;
b) cam means disposed intermediate said output shaft and said support member for linearly displacing said support member in a direction substantially perpendicular to the first direction; and,
c) said cam means including at least a first cam surface secured to said output shaft and at least a second cam surface secured to said support member.

18. An apparatus as in claim 17, wherein:
a) said cam means includes a first pair of cam surfaces secured to said output shaft, one of said first pair of cam surfaces is spaced from the other along a vertical axis; and,
b) said cam means further includes a second pair of cam surfaces fixed to said support member, said second pair of cam surfaces are substantially aligned with respect to each other along a vertical axis.

19. An apparatus for removing debris from between and around teeth, comprising:
a) a main body member having first and second ends;
b) an operating head being disposed adjacent said first end of said main body member, said operating head including upper and lower surfaces;
c) flossing means operably associated with said operating head for removing debris from between and around teeth;
d) drive means operably associated with said flossing means for displacing said flossing means in at least a first direction; and,
e) stop means for restricting movement of said flossing means relative to teeth of an individual, said stop means being disposed intermediate said upper and lower surfaces of said operating head, said stop means including a retaining member and means for adjusting the position of said retaining member.

20. An apparatus as in claim 19, wherein:

a) said operating head includes at least first and second tines each having an upper and lower surface, said first tine is spaced from said second tine; and,
b) said stop means includes a bar and spring means operably associated therewith, said bar extends between said first and second tines, said spring means biases said bar toward said lower surfaces of said first and second tines.

21. An apparatus as in claim 19, wherein:
a) said drive means includes a speed control for controlling a rate of displacement of said flossing means.

22. An apparatus as in claim 19, wherein:
a) said operating head includes first and second tines and first and second pins disposed adjacent thereto; and,
b) an adjustable protective cover is operably associated with said first and second pins.

23. A method of removing debris from between and around teeth, comprising the steps of:
a) providing a main body member having first and second ends;
b) providing an operating head disposed adjacent the first end of the main body member, the operating head including upper and lower surfaces;
c) providing flossing means operably associated with the operating head for removing debris from between and around teeth;
d) providing drive means operably associated with the flossing means for displacing the flossing means in at least a first direction;
e) providing stop means for restricting movement of the flossing means in at least a first direction relative to the teeth of an individual; and,
f) providing means for adjustably positioning the stop means intermediate the upper and lower surfaces of the operating head.

24. A method as in claim 23, further including:
a) providing adjustment means for adjusting the position of the stop means relative to the upper and lower surfaces of the operating head.

25. A method as in claim 23, further including:
a) detachably connecting the operating head to the body member.

26. An apparatus for removing debris from around and between teeth, comprising:
a) a main body member having first and second ends;
b) an operating head being disposed adjacent said first end of said main body member;
c) flossing means operably associated with said operating head for removing debris from between and around teeth, said flossing means including a support member for supporting a flossing material;
d) a drive means operably associated with said flossing means for displacing said support member in at least a first direction; and
e) shielding means hingedly connected to said operating head for shielding said support member, said shielding means being adapted to be moved between a first position in which said shielding means covers said support member and a second position in which said shielding means is removed from said support member.

27. An apparatus as in claim 26, wherein:
a) said support member includes a pair of resilient pins for maintaining the flossing material taught.

* * * * *